(12) United States Patent
Cowley

(10) Patent No.: US 8,478,428 B2
(45) Date of Patent: Jul. 2, 2013

(54) HELICAL ELECTRODE FOR NERVE STIMULATION

(75) Inventor: Anthony W. Cowley, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 476 days.

(21) Appl. No.: 12/766,046

(22) Filed: Apr. 23, 2010

(65) Prior Publication Data

US 2011/0264182 A1    Oct. 27, 2011

(51) Int. Cl.
*A61N 1/05* (2006.01)

(52) U.S. Cl.
USPC .......................................................... 607/118

(58) Field of Classification Search
USPC .......................................................... 600/377
See application file for complete search history.

(56) References Cited

U.S. PATENT DOCUMENTS

| | | |
|---|---|---|
| 3,421,511 A | 1/1969 | Schwartz et al. |
| 3,760,812 A | 9/1973 | Timm et al. |
| 3,796,221 A | 3/1974 | Hagfors |
| 4,291,699 A | 9/1981 | Geddes et al. |
| 4,305,402 A | 12/1981 | Katims |
| 4,384,926 A | 5/1983 | Wagner |
| 4,407,303 A | 10/1983 | Akerstrom |
| 4,458,696 A | 7/1984 | Larimore |
| 4,459,989 A | 7/1984 | Borkan |
| 4,573,481 A * | 3/1986 | Bullara ............... 607/118 |
| 4,590,946 A * | 5/1986 | Loeb ............... 600/375 |
| 4,592,359 A | 6/1986 | Galbraith |
| 4,606,349 A | 8/1986 | Livingston et al. |
| 4,608,985 A | 9/1986 | Crish et al. |
| 4,612,934 A | 9/1986 | Borkan |
| 4,628,942 A | 12/1986 | Sweeney et al. |
| 4,630,615 A | 12/1986 | Yomtov |
| 4,649,936 A | 3/1987 | Ungar et al. |
| 4,702,254 A | 10/1987 | Zabara |
| 4,793,353 A | 12/1988 | Borkan |
| 4,821,724 A | 4/1989 | Whigham et al. |
| 4,827,932 A | 5/1989 | Ideker et al. |
| 4,850,356 A | 7/1989 | Heath |
| 4,860,616 A | 8/1989 | Smith |
| 4,867,164 A | 9/1989 | Zabara |
| 4,870,341 A | 9/1989 | Pihl et al. |
| 4,899,750 A | 2/1990 | Ekwall |
| 4,903,700 A | 2/1990 | Whigham et al. |
| 4,920,979 A | 5/1990 | Bullara |

(Continued)

FOREIGN PATENT DOCUMENTS

WO    WO 2004069330    8/2004

OTHER PUBLICATIONS

International Searching Authority, International Search Report and Written Opinion for International Application No. PCT/US2011/033632 dated Jun. 30, 2011.

(Continued)

*Primary Examiner* — Carl H Layno
*Assistant Examiner* — Paula J Stice
(74) *Attorney, Agent, or Firm* — Cyberonics, Inc.

(57) ABSTRACT

A helical electrode for nerve stimulation includes an insulative helical substrate, having an inner surface, configured to wrap around a nerve. An electrical conductor is disposed upon the inner surface of the substrate. The conductor defines a helix of about one revolution and produces an electric field in which an injected current in similar axons varies by no more than about 25%. The conductor may include tapered end sections, which may be counter-tapered.

20 Claims, 11 Drawing Sheets

U.S. PATENT DOCUMENTS

| | | |
|---|---|---|
| 4,964,407 A | 10/1990 | Baker, Jr. et al. |
| 4,969,468 A | 11/1990 | Byers et al. |
| 4,979,511 A | 12/1990 | Terry, Jr. |
| 5,003,975 A | 4/1991 | Hafelfinger et al. |
| 5,025,807 A | 6/1991 | Zabara |
| 5,095,905 A | 3/1992 | Klepinski |
| 5,111,815 A | 5/1992 | Mower |
| 5,137,020 A | 8/1992 | Wayne et al. |
| 5,137,021 A | 8/1992 | Wayne et al. |
| 5,139,028 A | 8/1992 | Steinhaus et al. |
| 5,146,920 A | 9/1992 | Yuuchi et al. |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,201,808 A | 4/1993 | Steinhaus et al. |
| 5,201,865 A | 4/1993 | Kuehn |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,237,991 A | 8/1993 | Baker, Jr. et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,515 A | 7/1994 | Rutecki et al. |
| 5,335,657 A | 8/1994 | Terry, Jr. et al. |
| 5,351,394 A | 10/1994 | Weinberg |
| 5,411,528 A | 5/1995 | Miller et al. |
| 5,431,692 A | 7/1995 | Hansen et al. |
| 5,466,255 A | 11/1995 | Franchi |
| 5,501,702 A | 3/1996 | Plicchi et al. |
| 5,507,786 A | 4/1996 | Morgan et al. |
| 5,522,865 A | 6/1996 | Schulman et al. |
| 5,531,778 A | 7/1996 | Maschino et al. |
| 5,534,018 A | 7/1996 | Wahlstrand et al. |
| 5,540,730 A | 7/1996 | Terry, Jr. et al. |
| 5,540,734 A | 7/1996 | Zabara |
| 5,549,646 A | 8/1996 | Katz et al. |
| 5,571,150 A | 11/1996 | Wernicke et al. |
| 5,575,813 A | 11/1996 | Edell et al. |
| 5,620,474 A | 4/1997 | Koopman |
| 5,658,318 A | 8/1997 | Stroetmann et al. |
| 5,690,681 A | 11/1997 | Geddes et al. |
| 5,700,282 A | 12/1997 | Zabara |
| 5,707,400 A | 1/1998 | Terry, Jr. et al. |
| 5,713,936 A | 2/1998 | Staub et al. |
| 5,741,311 A | 4/1998 | Mc Venes et al. |
| 5,743,860 A | 4/1998 | Hively et al. |
| 5,755,742 A | 5/1998 | Schuelke et al. |
| 5,755,747 A | 5/1998 | Daly et al. |
| 5,759,199 A | 6/1998 | Snell et al. |
| 5,769,873 A | 6/1998 | Zadeh |
| 5,796,044 A | 8/1998 | Cobian et al. |
| 5,814,088 A | 9/1998 | Paul et al. |
| 5,876,425 A | 3/1999 | Gord et al. |
| 5,891,179 A | 4/1999 | Er et al. |
| 5,897,577 A | 4/1999 | Cinbis et al. |
| 5,916,239 A | 6/1999 | Geddes et al. |
| 5,919,220 A | 7/1999 | Stieglitz et al. |
| 5,928,272 A | 7/1999 | Adkins et al. |
| 5,995,868 A | 11/1999 | Osorio et al. |
| 6,035,237 A | 3/2000 | Schulman et al. |
| 6,052,624 A | 4/2000 | Mann |
| 6,073,050 A | 6/2000 | Griffith |
| 6,104,956 A | 8/2000 | Naritoku et al. |
| 6,154,678 A | 11/2000 | Lauro |
| 6,171,239 B1 | 1/2001 | Humphrey |
| 6,181,969 B1 | 1/2001 | Gord |
| 6,208,902 B1 | 3/2001 | Boveja |
| 6,212,431 B1 | 4/2001 | Hahn et al. |
| 6,216,045 B1 | 4/2001 | Black et al. |
| 6,259,951 B1 | 7/2001 | Kuzma et al. |
| 6,269,270 B1 | 7/2001 | Boveja |
| 6,304,787 B1 | 10/2001 | Kuzma et al. |
| 6,317,633 B1 | 11/2001 | Jorgenson et al. |
| 6,339,725 B1 | 1/2002 | Naritoku et al. |
| 6,341,236 B1 | 1/2002 | Osorio et al. |
| 6,393,325 B1 | 5/2002 | Mann et al. |
| 6,400,988 B1 | 6/2002 | Gurewitsch |
| 6,418,348 B1 | 7/2002 | Witte |
| 6,445,951 B1 | 9/2002 | Mouchawar |
| 6,453,198 B1 | 9/2002 | Torgerson et al. |
| 6,456,481 B1 | 9/2002 | Stevenson |
| 6,473,653 B1 | 10/2002 | Schallhorn et al. |
| 6,477,417 B1 | 11/2002 | Levine |
| 6,490,486 B1 | 12/2002 | Bradley |
| 6,505,074 B2 | 1/2003 | Boveja et al. |
| 6,510,332 B1 | 1/2003 | Greenstein |
| 6,529,774 B1 | 3/2003 | Greene |
| 6,553,263 B1 | 4/2003 | Meadows et al. |
| 6,556,868 B2 | 4/2003 | Naritoku et al. |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,600,957 B2 | 7/2003 | Gadsby |
| 6,606,523 B1 | 8/2003 | Jenkins |
| 6,609,025 B2 | 8/2003 | Barrett et al. |
| 6,620,186 B2 | 9/2003 | Saphon et al. |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,648,823 B2 | 11/2003 | Thompson |
| 6,658,294 B1 | 12/2003 | Zadeh et al. |
| 6,662,053 B2 | 12/2003 | Borkan |
| 6,671,556 B2 | 12/2003 | Osorio et al. |
| 6,684,105 B2 | 1/2004 | Cohen et al. |
| 6,687,538 B1 | 2/2004 | Hrdlicka et al. |
| 6,690,974 B2 | 2/2004 | Archer et al. |
| 6,711,440 B2 | 3/2004 | Deal et al. |
| 6,718,203 B2 | 4/2004 | Weiner et al. |
| 6,718,207 B2 | 4/2004 | Connelly |
| 6,721,600 B2 | 4/2004 | Jorgenson et al. |
| 6,721,603 B2 | 4/2004 | Zabara et al. |
| 6,725,092 B2 | 4/2004 | MacDonald et al. |
| 6,731,979 B2 | 5/2004 | MacDonald |
| 6,745,077 B1 | 6/2004 | Griffith et al. |
| 6,754,539 B1 | 6/2004 | Erickson et al. |
| 6,757,566 B2 | 6/2004 | Weiner et al. |
| 6,760,624 B2 | 7/2004 | Anderson et al. |
| 6,760,625 B1 | 7/2004 | Kroll |
| 6,760,628 B2 | 7/2004 | Weiner et al. |
| 6,763,268 B2 | 7/2004 | MacDonald et al. |
| 6,778,856 B2 | 8/2004 | Connelly et al. |
| 6,792,316 B2 | 9/2004 | Sass |
| 6,795,730 B2 | 9/2004 | Connelly et al. |
| 6,795,736 B2 | 9/2004 | Connelly et al. |
| 6,799,069 B2 | 9/2004 | Weiner et al. |
| 6,804,557 B1 | 10/2004 | Kroll |
| 6,819,954 B2 | 11/2004 | Connelly |
| 6,819,958 B2 | 11/2004 | Weiner et al. |
| 6,829,509 B1 | 12/2004 | MacDonald et al. |
| 6,843,870 B1 | 1/2005 | Bluger |
| 6,845,266 B2 | 1/2005 | Weiner et al. |
| 6,850,805 B2 | 2/2005 | Connelly et al. |
| 6,875,180 B2 | 4/2005 | Weiner et al. |
| 6,901,290 B2 | 5/2005 | Foster et al. |
| 6,906,256 B1 | 6/2005 | Wang |
| 6,907,295 B2 | 6/2005 | Gross et al. |
| 6,920,357 B2 | 7/2005 | Osorio et al. |
| 6,925,328 B2 | 8/2005 | Foster et al. |
| 6,944,489 B2 | 9/2005 | Zeijlemaker et al. |
| 6,949,929 B2 | 9/2005 | Gray et al. |
| 6,954,674 B2 | 10/2005 | Connelly |
| 6,961,618 B2 | 11/2005 | Osorio et al. |
| 6,985,775 B2 | 1/2006 | Reinke et al. |
| 6,993,387 B2 | 1/2006 | Connelly et al. |
| 7,006,859 B1 | 2/2006 | Osorio et al. |
| 7,010,357 B2 | 3/2006 | Helfer et al. |
| 7,013,174 B2 | 3/2006 | Connelly et al. |
| 7,015,393 B2 | 3/2006 | Weiner et al. |
| 7,047,074 B2 | 5/2006 | Connelly et al. |
| 7,054,686 B2 | 5/2006 | MacDonald |
| 7,107,097 B2 | 9/2006 | Stern et al. |
| 7,123,013 B2 | 10/2006 | Gray |

| | | |
|---|---|---|
| 7,171,166 B2 | 1/2007 | Ng et al. |
| 7,174,219 B2 | 2/2007 | Wahlstrand et al. |
| 7,212,869 B2 | 5/2007 | Wahlstrom et al. |
| 7,221,981 B2 | 5/2007 | Gliner |
| 7,239,924 B2 | 7/2007 | Kolberg |
| 7,289,856 B1 | 10/2007 | Karicherla |
| 7,584,004 B2 | 9/2009 | Caparso et al. |
| 7,797,058 B2 * | 9/2010 | Mrva et al. .................. 607/118 |
| 2002/0072782 A1 | 6/2002 | Osorio et al. |
| 2003/0083726 A1 | 5/2003 | Zeijlemaker et al. |
| 2003/0195601 A1 | 10/2003 | Hung et al. |
| 2004/0010303 A1* | 1/2004 | Bolea et al. .................. 607/118 |
| 2004/0015205 A1 | 1/2004 | Whitehurst et al. |
| 2004/0147992 A1 | 7/2004 | Bluger et al. |
| 2004/0167583 A1 | 8/2004 | Knudson et al. |
| 2004/0172088 A1 | 9/2004 | Knudson et al. |
| 2004/0210291 A1 | 10/2004 | Erickson |
| 2005/0015128 A1 | 1/2005 | Rezai et al. |
| 2005/0016657 A1 | 1/2005 | Bluger |
| 2005/0107858 A1 | 5/2005 | Bluger |
| 2005/0154426 A1 | 7/2005 | Boveja et al. |
| 2005/0154435 A1 | 7/2005 | Stern et al. |
| 2005/0222642 A1 | 10/2005 | Przybyszewski et al. |
| 2005/0272280 A1 | 12/2005 | Osypka |
| 2006/0058597 A1 | 3/2006 | Machado et al. |
| 2006/0106430 A1 | 5/2006 | Fowler et al. |
| 2006/0167497 A1 | 7/2006 | Armstrong et al. |
| 2006/0173493 A1 | 8/2006 | Armstrong et al. |
| 2006/0184211 A1 | 8/2006 | Gaunt et al. |
| 2006/0224199 A1 | 10/2006 | Zeijlemaker et al. |
| 2006/0253164 A1 | 11/2006 | Zhang et al. |
| 2006/0265025 A1 | 11/2006 | Goetz et al. |
| 2007/0027497 A1 | 2/2007 | Parnis et al. |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0060991 A1 | 3/2007 | North et al. |
| 2007/0073150 A1 | 3/2007 | Gopalsami et al. |
| 2007/0100392 A1 | 5/2007 | Maschino et al. |
| 2007/0100406 A1 | 5/2007 | Kollatschny et al. |
| 2007/0142889 A1 | 6/2007 | Whitehurst et al. |
| 2007/0173902 A1 | 7/2007 | Maschino et al. |
| 2007/0179557 A1 | 8/2007 | Maschino et al. |
| 2007/0179579 A1 | 8/2007 | Feler et al. |
| 2007/0179584 A1 | 8/2007 | Gliner |
| 2008/0027524 A1* | 1/2008 | Maschino et al. ............ 607/118 |
| 2008/0033503 A1 | 2/2008 | Fowler et al. |
| 2008/0046035 A1 | 2/2008 | Fowler et al. |
| 2008/0071323 A1 | 3/2008 | Lowry et al. |
| 2008/0200925 A1 | 8/2008 | Johnson |
| 2008/0215110 A1 | 9/2008 | Gunderson et al. |
| 2008/0255582 A1 | 10/2008 | Harris |
| 2009/0076567 A1 | 3/2009 | Fowler et al. |
| 2009/0149912 A1 | 6/2009 | Dacey, Jr. et al. |

OTHER PUBLICATIONS

Basser, Peter J. et al., "New Currents in Electrical Stimulation of Excitable Tissues," Annu Rev. Biomed. Eng., Annu., 2000, 02:377-97.

Sahin, Mesut et al., "Improved Nerve Cuff Electrode Recordings With Subthreshold Anodic Currents," IEEE Transactions on Biomedical Engineering, vol. 45, No. 8, Aug. 1998, 1044-1050.

Woodbury, J. Walter et al., "Vagal Stimulation Reduces the Severity of Maximal Electroshock Seizures in Intact Rats: Use of a Cuff Electrode for Stimulating and Recordiing," PACE, vol. 14, Jan. 1991, 94-107.

* cited by examiner

HELICAL ELECTRODE FOR NERVE STIMULATION

BACKGROUND OF THE INVENTION

1. Field of the Invention

The present disclosure generally relates to electrodes that are used in nerve stimulation. More particularly, the present disclosure relates to helical electrodes for nerve stimulation, such as vagus nerve stimulation.

2. Description of the Related Art

Since its introduction, nerve stimulation has been used to treat a variety of neurological conditions. Vagus Nerve Stimulation (VNS) is one type of nerve stimulation that has been used as a treatment for intractable epilepsy. Typically, this involves stimulating the left cervical vagus nerve via an implanted electrode (the vagus nerve can also be stimulated outside of the cervical area and on the right vagus). VNS has been available for clinical treatment of epilepsy in the U.S. since 1997. The therapy is achieved through an implanted pulse generator that delivers a bipolar, biphasic pulse. The implant procedure is very similar to the implantation of a pacemaker. The generator is implanted subcutaneously, typically in the upper left chest wall. An electric lead is connected between the pulse generator and the electrode using a subcutaneous tunneling tool to the vagus nerve, which lies in the carotid sheath.

Traditional nerve stimulation electrodes utilize a nerve cuff (a cylinder with an open side) that is placed around the nerve and sutured closed. In recent years, helical electrodes have been developed as an alternative to the nerve cuff because they provide a "self-sizing" feature by allowing the electrode to expand and contract to account for post-implant inflammation and ingrowth of fibrotic tissue between the nerve and electrode without increasing pressure on the nerve. Current VNS electrodes are frequently fabricated from a platinum-iridium alloy embedded in flexible silicon. The electrodes are helical in shape, and consist of an anode, a cathode and a tether helical (which serves to anchor the anode and cathode but does not itself contain an embedded metal electrode).

It is desirable for helical electrodes to provide effective nerve stimulation with minimum power consumption. It is believed that current electrodes fall short in this area. The present disclosure is directed to overcoming, or at least reducing the effects, of one or more of the issues set forth above.

SUMMARY OF THE INVENTION

It has been recognized that it would be advantageous to develop a nerve stimulation system which elicits maximal stimulation of nerve fibers in order to achieve a therapeutic effect.

It has also been recognized that it would be advantageous to develop a nerve stimulation system that improves the efficacy of treatment while also conserving pulse generator battery power.

In accordance with one aspect thereof, the present disclosure provides a helical electrode for nerve stimulation. The electrode includes an insulative helical substrate, having an inner surface, configured to wrap around a nerve. An electrical conductor is disposed upon the inner surface, the conductor defining a helix of about one revolution. The conductor produces an electric field in which an injected current in similar axons varies by no more than about 25%. The conductor may produce an electric field in which the injected current in similar axons may vary by no more than about 10%.

Axons may be considered similar if the axons reside in a similar location and are of a similar axon type. An axon may be considered to reside in a similar location if they are approximately equidistant from the electrical conductor, are approximately equidistant and orthogonal from the electrical conductor, or are approximately equidistant from the longitudinal axis of the nerve. Axons may be considered to be of a similar type if they are the same axon type or nerve fiber type, are axons with approximately the same degree of myelination, or are axons that have a diameter that varies by no more than 2 μm.

The electrical conductor may also include tapered end sections, which may be counter-tapered. The tapered section of the conductor may be approximately one fourth of the length of the conductor and may reduce the width of the conductor by about one eighth. The end sections of the conductor may also be truncated. The helix of the electrode may have a pitch from approximately 1 mm per turn to 2.5 mm per turn with a central aperture having a diameter from about 2 mm to about 3 mm. The helix of the conductor may be more than one revolution before implantation to accommodate post-implantation expansion of the nerve. The conductor may be comprised of various materials such as platinum, platinum/iridium alloy, iridium oxide, titanium nitride, tantalum, and tantalum oxide.

In accordance with another aspect thereof, the present disclosure provides a helical electrode for nerve stimulation. The electrode comprises an insulative helical substrate having an inner surface configured to substantially wrap around an entire circumference of a nerve. The entire circumference of the nerve may be divided into a plurality of equal sectors the conductor produces an electric filed in which the peak value of the second spatial derivative of the electric field applied in each of the equal sectors varies by no more than about 25%. Further, the peak valve of the second spatial derivative of the electric field applied in each of the equal sectors may vary by no more than about 10%.

In accordance with yet another aspect thereof, the disclosure provides a helical electrode for nerve stimulation. The electrode includes an insulative helical substrate, having an inner surface, configured to wrap around a nerve. An electrical conductor is disposed on the inner surface so as to be adjacent to the nerve. The electrical conductor is a helix of about one revolution and includes tapered end sections.

These and other embodiments of the present application will be discussed more fully in the description. The features, functions, and advantages can be achieved independently in various embodiments of the claimed invention, or may be combined in yet other embodiments.

Figure 1:
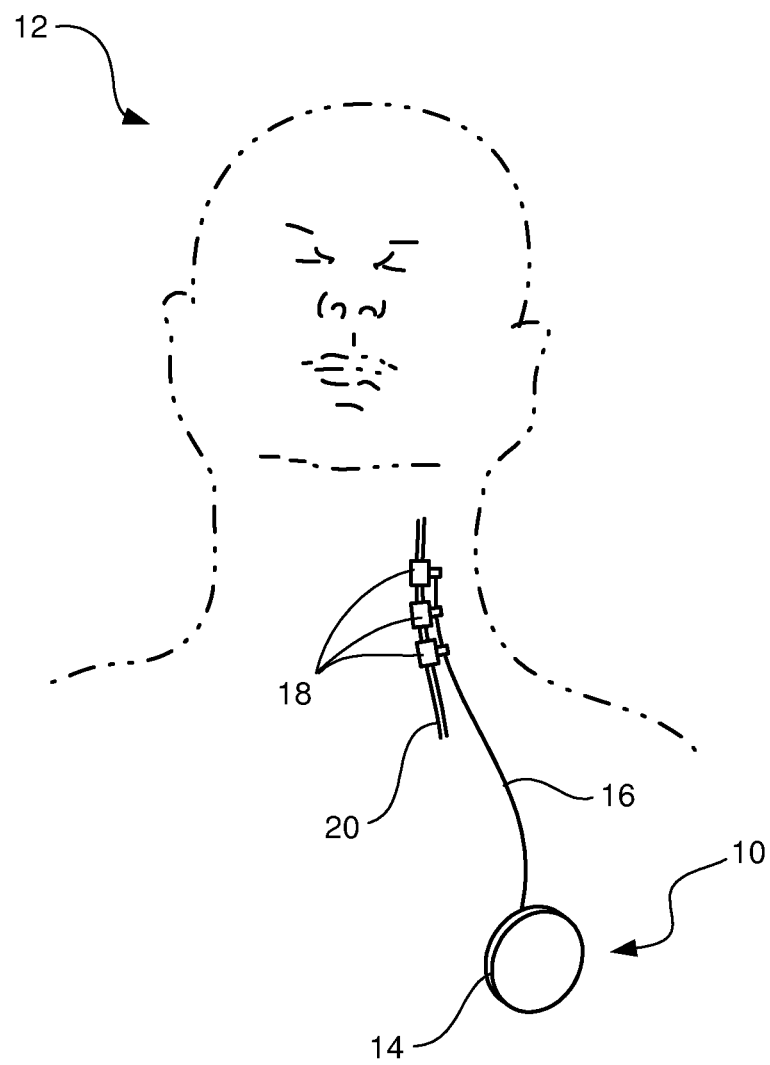
FIG. 1 is a schematic representation of a human subject showing the placement of a subcutaneous pulse generator and nerve stimulation electrode attached at the left vagus nerve in one embodiment of a nerve stimulation system.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope as defined by the appended claims.

Description of Illustrative Embodiments

Illustrative embodiments are described below as they might be employed in a helical electrode for nerve stimulation, and a system employing the same. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Further aspects and advantages of the various embodiments will become apparent from consideration of the following description and drawings. These embodiments are described in sufficient detail to enable those skilled in the art to practice the invention, and it is to be understood that modifications to the various disclosed embodiments may be made, and other embodiments may be utilized, without departing from the spirit and scope of the present invention. The following detailed description is, therefore, not to be taken in a limiting sense.

VNS was approved by the FDA in 1998 as an adjunctive therapy for epilepsy with partial onset seizures. Of people diagnosed with epilepsy, 20-30% will have medically intractable epilepsy, meaning their seizures cannot be controlled by antiepileptic drugs alone. VNS is used in combination with drugs to help bring relief to some of these patients. One objective of VNS therapy is to elicit maximal stimulation of the afferent A fibers in the vagus nerve in order to achieve a therapeutic effect. There are several reasons why maximal stimulation of these fibers is required for the treatment. First, because the causes of epilepsy are varied and not well understood, selective stimulation of a group of fibers to affect only a certain portion of the brain would likely not be feasible. Also, unlike with stimulation of motor neurons, there is no easily measured response to stimulation, making it difficult to determine which fibers are being stimulated during implantation of the device. Lastly, the low incidence of side effects associated with VNS suggests that maximal stimulation of the afferent A fibers is well tolerated.

There have been several studies related to the safety of helical electrodes used in nerve stimulation. However, there has been little work done to investigate the electric field within the nerve created by helical electrodes and the field's ability to stimulate, or recruit, the nerve fibers. The inventor has recognized that a better understanding of the electric field and its effect on nerve stimulation is desirable to evaluate the effectiveness of the electrodes and suggest design improvements. In particular, the electric field created by VNS electrodes has a significant effect on the efficacy of treatment and electrical power usage of these devices. It has been determined that stimulation of a nerve is dependent upon the second derivative of the electric field in the longitudinal direction (along the length of the nerve). Consequently, it is desirable that the change in the electric field be concentrated in the longitudinal direction, and electrodes that concentrate the change in the electric field in this way will be more effective.

As disclosed herein, a nerve stimulation electrode has been developed having a similar shape to prior electrodes used for VNS, but incorporates changes to the current-carrying conductor. The conductor substantially completely encircles the nerve, and the ends of the conductor can include a taper. This taper can cause the ribbon to come to sharp points at the ends, or the ends can be flattened or truncated.

A schematic diagram of one embodiment of a neurocybernetic prosthesis (NCP), indicated generally at 10, implanted in a patient 12 is shown in FIG. 1. The NCP 10 contains two main components, a pulse generator 14 and a tether 16 which provides the interface between the pulse generator and one or more electrodes 18, which are implanted around the vagus nerve 20. The tether and electrodes are collectively referred to as the lead. An NCP of this type is known to those of skill in the art, and is commercially available, such as from Cyberonics, Inc. of Houston, Tex. The pulse generator can be a multi-programmable device, which allows a physician to control several parameters. In one embodiment, the programmable parameters are signal amplitude (e.g. 0-3.5 mA), frequency (e.g. 1-30 Hz), pulse width (e.g. 130-1000 μs), signal ON time (e.g. 7-60 sec) and signal OFF time (e.g. 0.2-180 min). It is to be appreciated that these pulse parameters are only exemplary, and that other parameters and ranges can be used. The pulse generator can stimulate in an "open loop" mode based on a predetermined stimulation schedule or stimulate in a "closed loop" mode responding to a detected or predicted event. The event triggering a closed loop stimulation can be based on, for example: EEG, ECoG, or other brain signals; ECG, heart rate variability, blood pressure or other heart or cardiovascular signals; muscle signals such as EMG; time or circadian rhythms; neural activity in cranial or peripheral nerves; body temperature and temperature variations; tissue impedance; and other physiological or pathological changes.

The pulses can be delivered at the specified amplitude and frequency over the course of the ON time, and then during the OFF time, no stimulation takes place. This type of device typically does not stimulate continuously because it has been found that the antiepileptic effect tends to last much longer than the actual time of stimulation. In one embodiment, pulse settings can be 2 mA, at 15 Hz frequency, 250 µs pulse width, with a 30 sec ON time, and 5 min OFF time. The variability in parameters allows for the physician to adjust for greater efficacy or less severe side effects, depending on the patient.

Figure 2:
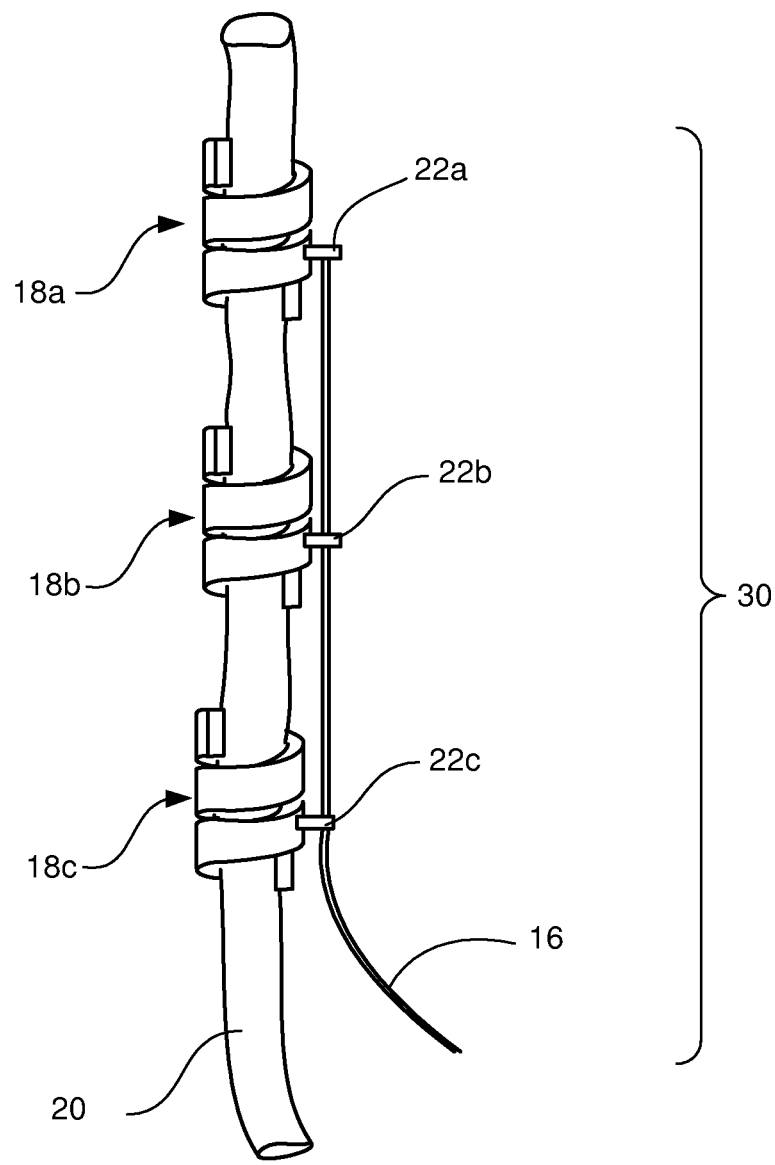
FIG. 2 is a pictorial representation of a group of two helical stimulation electrodes and one anchoring helix attached along a nerve in one embodiment of a nerve stimulation system.

A pictorial representation of a distal end section of a lead 30 in one embodiment of a nerve stimulation system is provided in FIG. 2. In this embodiment, the lead includes three helical devices 18 attached axially along a nerve 20. Each of the helical devices is interconnected to the pulse generation device (14 in FIG. 1) via the tether 16. This embodiment includes two helical electrodes 18a, 18b, and a third helical device 18c that is electrically inactive, but which is attached to the tether and provides additional support to anchor the electrodes to the nerve. Each of the helices includes a post 22, which mechanically connects the helix to the tether 16. In the electrically active helices (18a, b), this post is also an electrical conductor, which extends through the substrate of the helix and connects to the conductor portion of the electrode on the inner surface of the helix, to transmit electrical pulses thereto. For the third helix, 18c, the post provides a mechanical connection only, not an electrical connection, serving to anchor the electrodes better to the nerve. This third anchoring helix 18c may be longer than helices 18a and 18b to anchor lead 30 to the nerve more securely. In vagus nerve stimulation, these three helices can be wrapped around the mid-cervical portion of the vagus nerve, inferior to the cardiac branches of the left vagus nerve. In another embodiment, helix 18c is also an electrically conductive electrode. In other embodiments, multiple electrodes (e.g., three, four, five, or more) can be used to stimulate the nerve with various afferent and/or efferent stimulation patterns by adjusting the timing and amount of current or voltage applied to the electrodes and selecting which electrodes are used. In further embodiments, the site of the stimulation is other than the left mid-cervical vagus (e.g., right vagus, near the cardiac plexus, or other nerves aside from the vagus large enough to wrap an electrode around). In still further embodiments, the electrode is a cylinder cuff electrode or other shape wrapping around the targeted nerve.

Figure 3:
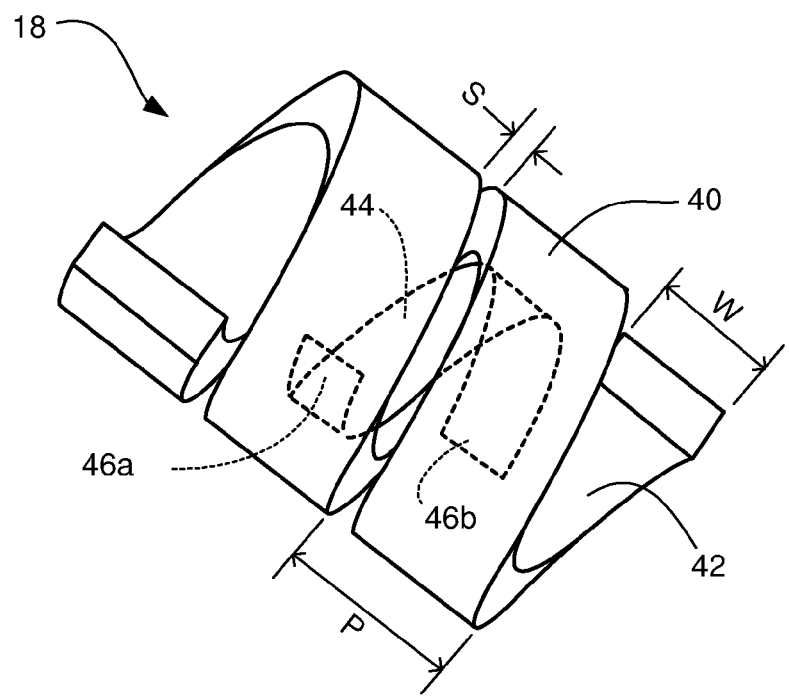
FIG. 3 is a perspective view of an embodiment of a helical electrode suitable for nerve stimulation.

A perspective view of an embodiment of a helical electrode 18 suitable for vagus nerve stimulation is provided in FIG. 3. The electrode generally comprises an insulating substrate 40 that is helical in shape and defines an inner surface 42. The substrate can be made from a silicon elastomer or other suitable biocompatible insulative material. Flexibility of the substrate facilitates implantation, and also provides the "self-sizing" feature mentioned above. In one embodiment, the substrate has a width W that is about 1.4 mm, is about 0.9 mm thick, and defines about 2½ turns in total, with an inner diameter of about 2 mm to 3 mm, to accommodate for variability in the diameter of the vagus nerve. With these dimensions, a total linear length of the substrate will be about 4 mm to 5 mm. Other sizes and ranges can also be used. The helical substrate also has a pitch P, which depends upon the width W of the substrate and the spacing S between adjacent turns of the helix. It will be appreciated that the pitch P will increase or decrease as W and S increase or decrease.

Fabricated upon or embedded within the interior surface 42 of the substrate 40 is a conductor 44. This conductor can be a ribbon of metal, and provides the direct electrical stimulation to the nerve, in response to pulses from the pulse generator. In one embodiment, the conductive ribbon has a width of about 0.75 mm, and is about 0.01 mm thick. The conductor can be of a variety of biocompatible conductive materials, including noble metals such as platinum, platinum/iridium alloy and iridium oxide, or other materials such as titanium nitride and tantalum/tantalum oxide. The conductor can be attached to or fabricated upon the substrate by a variety of known methods such as encapsulation, fusion welding, resistance welding, sputtering, or electrochemical growth.

The conductor 44 in FIG. 3 is of substantially constant width, and defines about one revolution about the helix. As used herein, the phrase "about one revolution" is used to mean anything more than a half revolution (180°) and less than one-and-a-half revolutions (540°). Due to the pitch P of the substrate, there is a longitudinal gap between opposing ends 46a, b of the conductor. The region of this longitudinal gap, where the opposing ends of the conductor approach each other, is referred to herein as the overlap area. Because of the helical geometry, the conductor ends do not physically overlap, but the electric fields that are produced by the ends of the conductor do tend to overlap. This phenomenon is illustrated in FIG. 4.

Figure 4:
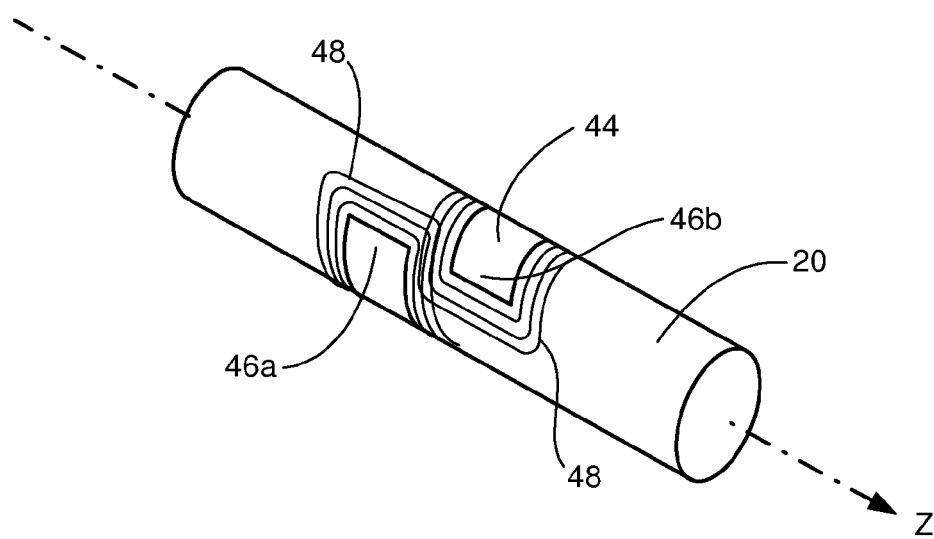
FIG. 4 is a perspective view of a portion of a nerve showing a non-tapered helical conductor and field lines representing interference of electric fields from the ends of the conductor in the overlap region.

Shown in FIG. 4 is an idealized portion of a nerve 20 with a helical conductor 44 (like that of FIG. 3) wrapped around it. The substrate (40 in FIG. 3) is not shown in this view for clarity. Radiating around the ends 46 of the conductor are field lines 48, representing the electric field produced by the ends of the conductor. As can be seen, these field lines overlap in the gap between the conductor ends. The interference between these two fields causes the electric field to be spread out along the Z-axis of the nerve in the overlap region (herein, the Z-axis refers to the longitudinal axis, or axis parallel to the direction of the nerve, as shown in FIG. 4). Unfortunately, this spreading effect tends to reduce the recruitment of nerve fibers near the overlap area, which reduces the efficacy of nerve stimulation, as discussed in more detail below.

Figure 5:
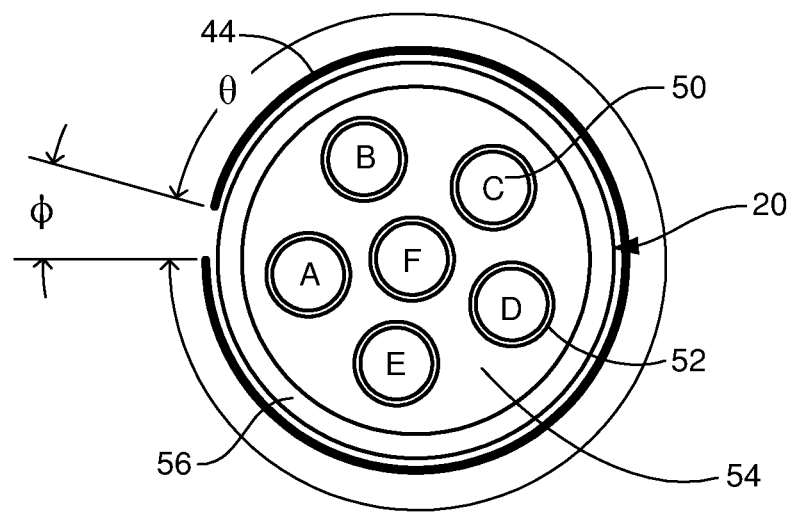
FIG. 5 is a cross-sectional view of a nerve, showing a stimulation electrode wrapped less than 360° around the nerve.
Figure 6:
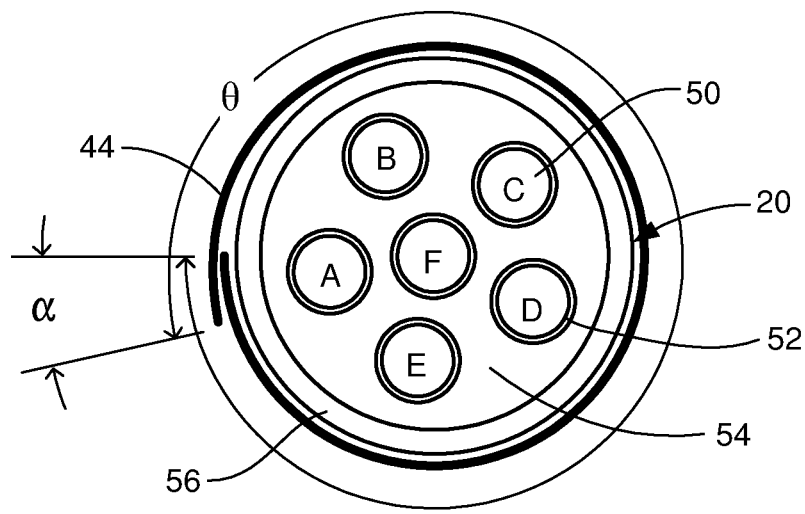
FIG. 6 is a cross-sectional view of a nerve, showing a stimulation electrode wrapped more than 360° around the nerve.

FIGS. 5 and 6 show two idealized cross-sectional views of a nerve 20 representing the left vagus nerve, with a helical electrode 44 wrapped around the nerve some amount less than 360° (FIG. 5), and some amount greater than 360° (FIG. 6). The interior of the nerve includes six fascicles 50, labeled A-F, each surrounded by a layer of perineurium 52. The fascicles contain the individual nerve fibers or neurons. Each fascicle contains several thousand neurons. The terms nerve fiber and neuron are used interchangeably herein. The fascicles include outer fascicles, A-E, closer to the perimeter of the nerve, and a central fascicle F which is near the center of the nerve. The region between the fascicles comprises epineurium 54, and a layer of connective tissue 56 surrounds the entire nerve 20.

Naturally, the size of these anatomical features may vary from person to person, but typical sizes and size ranges are well known. Furthermore, it is to be appreciated that the representation in FIGS. 5 and 6 is idealized, and that actual fascicles can be irregular in shape, size and positioning due to normal anatomical variations. The mid-cervical vagus nerve (i.e., the vagus nerve in the location where the VNS electrode is typically applied) in most humans contains between 8 and 12 fascicles of varying size with a total of 80,000-100,000 neurons distributed within them. Several of these fascicles can be quite small, and are therefore not illustrated in the idealized models of FIGS. 5 and 6. This approximation of the features of the vagus nerve helps to make the analysis of many electrode configurations more computationally tractable. However, the idealized model provides a useful approximation of the nerve configuration. The inventor has created a finite element model of the vagus nerve and helical electrode described above using representative sizes and known characteristics for the anatomical features of the nerve, in order to analyze the effects of electrode geometry on stimulation of the nerve, as discussed below.

The inventor determined that it is desirable to concentrate the electric field near the ends of the ribbon. While investigating the geometry of the helical conductor and its effects on the electric field generated in the nerve and the relative effectiveness of different conductor designs, the inventor has determined that the neurons located within fascicles 50 nearest the overlap area are the most sensitive to changes in electrode length. In FIGS. 5 and 6 the fascicle nearest the overlap area is fascicle A. This sensitivity to electrode length is believed to be due to overlap in the electric fields created by the ends of the conductor, as illustrated in FIG. 4. The resultant field covers a larger longitudinal distance along the longitudinal axis of the nerve (the Z-axis in FIG. 4), and because fiber recruitment is most effective with a highly concentrated change in the electric field along the length of the nerve, the fibers located in this area are harder to recruit because the applied electric field and amount of current injected at this overlap area is weaker and varied from other areas.

Figure 7:
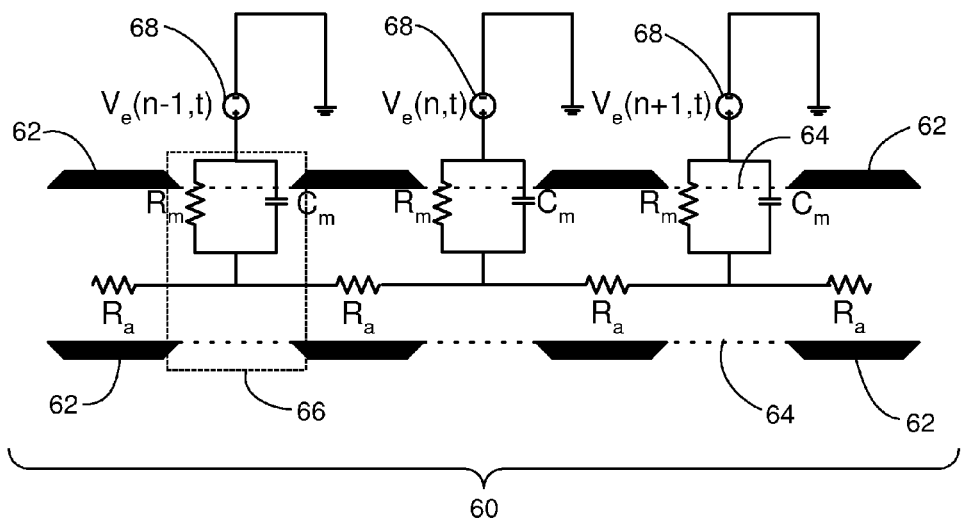
FIG. 7 is a schematic diagram representing an equivalent circuit model for a section of a neuron.

As noted above, nerve recruitment or stimulation is a function of the second derivative of the electric field in the longitudinal direction of a given axon. This second spatial derivative of the electric field is referred to as "injected current" and it represents the current flow into an individual neuron caused by the electric field created by the electrodes. In order to analyze the effect of injected current, the inventor has modeled the axon as an equivalent electrical circuit. Provided in FIG. 7 is an equivalent circuit model for a section of the axon 60 of a neuron. In FIG. 7, the solid blocks 62, in opposing pairs, represent the extent of individual Schwann cells 62 that are present along the axon 60. The opposing dotted lines 64 connecting the solid blocks 62 represent the cell membrane of the neuron. The space between the cell membranes represents the intracellular region, and the area outside the membrane lines represents extracellular regions.

In myelinated axons, Schwann cells 62 form a myelin sheath, which is an electrically insulating (i.e. dielectric) material that forms a layer around the axon of the neuron. The gaps between adjacent Schwann cells are called the nodes of Ranvier, indicated at 66. Nodes of Ranvier 66 are the gaps (approximately 1 micrometer in length) formed between the myelin sheaths generated by adjacent Schwann cells 62. At nodes of Ranvier 66, the cell membrane along the axon is uninsulated and therefore capable of generating electrical activity. The diagram of FIG. 7 represents each node of Ranvier 66, enumerated with the variable n, as an RC circuit, with a membrane resistance $R_m$, and a membrane capacitance $C_m$. The resistance $R_a$ represents axoplasm resistance, or the resistance to electrical current of the axon of the neuron between adjacent nodes of Ranvier. The value $V_e(n, t)$ represents a time dependent extracellular voltage that is applied at node n.

The circuit model shown in FIG. 7 has been used to model a section of a neuron using Kirchoff's Current Law (KCL) at each node. Writing Kirchoff's Current Law at node n and rearranging gives:

$$C_m \frac{dV_m(n,t)}{dt} + G_m V_m(n,t) - \qquad [1]$$
$$G_a[V_m(n-1,t) - 2V_m(n,t) + V_m(n+1,t)] =$$
$$G_a[V_e(n-1,t) - 2V_e(n,t) + V_e(n+1,t)]$$

The right hand side of this equation is the "injected current." In this equation, $G_m$ represents the membrane conductance, $G_a$ represents the axoplasm conductance, $V_m(n,t)$ represents a time dependent transmembrane potential at node n, and $V_e(n,t)$ represents a time dependent extracellular voltage at node n. The extracellular voltage Ve at each node is represented by the voltage sources 68 in FIG. 7. The axoplasm conductance $G_a$ is given by the following equation:

$$G_a = \frac{\pi d^2}{4\rho_a L} \qquad [2]$$

In this equation, $\rho_a$ is the axoplasm resistivity, d is the axon diameter, and L is the intermodal length, or the physical distance between nodes of Ranvier along the axon. Substituting equation [2] into equation [1], the right hand side of equation [1] can be rewritten as follows:

$$I(n,t) = \frac{\pi d^2 [V_e(n-1,t) - 2V_e(n,t) + V_e(n+1,t)]}{4\rho_a L} \qquad [3]$$

This equation is the second difference in the electric field over an internodal length L. This physical distance L is typically on the order of 100 microns. Consequently, since L is very small, equation [3] becomes analogous to the second spatial derivative of the electric field along the length of the neuron. This equation gives the injected current value.

Figure 8:
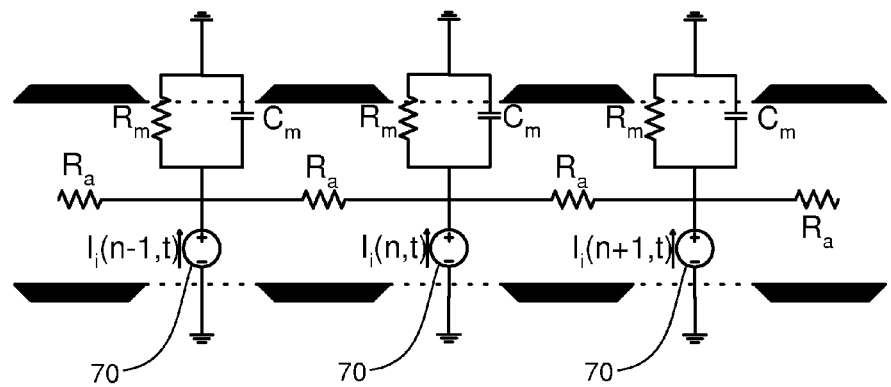
FIG. 8 is a schematic diagram representing the circuit model of FIG. 7, with the extracellular voltage sources replaced by an intracellular current source representing injected current.

It will be noted that the left side of equation [3] gives a current $I_i(n,t)$ at node n, rather than a voltage. Because the electrode disclosed herein produces an electric field within the axon of the nerve, the extracellular voltage sources $V_e$ in the circuit diagram of FIG. 7 can be replaced by equivalent intracellular current sources $I_i$ with values calculated from equation [3]. A new circuit diagram with the external voltage sources replaced by internal current sources 70 is provided in FIG. 8. The two circuit diagrams of FIGS. 7 and 8 will be equivalent so long as the injected current sources are assigned values according to equation [3]. The inventor has made this assumption to simplify the circuit equations and make them easier to solve numerically. The physical implication of this assumption, which is believed to be valid, is that the value of each injected current source is actually the amount of current flowing into the cell at a particular node.

It is believed that there is no way to directly measure injected current in a nerve of a living subject. Due to variations in individual anatomy, and uncertainty about the mechanism of action of the antiepileptic effect of vagus nerve stimulation therapy, it is believed that there is no way to definitively determine whether the specific nerve fibers that produce an antiepileptic effect are being excited after the electrode has been implanted. Therefore, the goal of VNS is maximal excitation of the nerve fibers within the vagus nerve trunk. Consequently, the geometric characteristics of the electrode are believed to be relevant factors in effectively controlling seizures with minimal side effects. In order to improve the VNS electrode, it is desirable to decrease the sensitivity near the overlap area as much as possible.

The cause of the decreased stimulation near this overlap area is due in part to the helical geometry of the electrode. FIGS. 5 and 6 show two generalized cases related to the angular or circumferential length of the helical electrode 44. Where the angular length θ of the electrode is less than 360°, (FIG. 5) this leaves an angular gap Φ between the electrode ends 46. Where the angular length θ of the electrode is greater than 360°, (FIG. 6) this creates an angular overlap a of the electrode ends 46. It is to be understood that the representation in FIG. 6 is illustrative only, and represents the angular extent of the electrode. However, the conductor 44 does not actually overlap itself because of the longitudinal gap or offset produced by the helical geometry (i.e., the ends of the electrode are disposed at different Z-axis positions along the length of the nerve trunk). The configuration shown in FIG. 6 is intended only to represent the angular coverage provided by the electrode. It will be apparent that the circumferential overlap or gap in the electrode ends is a function of the length of the conductor and the diameter of the nerve, as well as of the helical pitch P of the conductor and substrate (i.e., a greater pitch P will reduce the overlap for a given length of conductor and a smaller pitch P will reduce the longitudinal offset between the two electrode ends).

The inventor has determined that where θ<360° (FIG. 5), most of the electric field produced in areas of the nerve away from the conductor ends 46 (i.e. nerve fibers farthest from the overlap area, such as fibers within fascicles C and D in FIGS. 5 and 6) is caused by current flowing out of the nearest portions of the electrode, and the change in the field is fairly concentrated along the axis of the nerve 20. However, in the overlap area near the gap Φ, the electric field created by each end 46 of the electrode begins to overlap, and the axial change in the field is more spread out due to the pitch P of the electrode. Thus the injected current for fibers near the overlap area (e.g. fibers in fascicle A in FIGS. 5 and 6) is lower than for fibers away from the overlap area. Further evidence of the decreased concentration of the change in the electric field has been observed when the electrode overlaps (θ>360°), as shown in FIG. 6. As the length of the conductor increases and more of the electrode overlaps circumferentially, the two fields created by these overlapping end sections 46 combine, resulting in less stimulation of the neurons near those areas. Also, the field overlap covers a larger circumferential distance when θ>360, therefore reducing the injected current for a large number of axons.

Of particular concern are the electric field applied to the outer axons in the overlap region (e.g. axons within fascicle A in FIGS. 5 and 6) and the outer axons in the region opposite the overlap (e.g. axons within fascicles C and D in FIGS. 5 and 6). Nerve recruitment improves when the applied field and injected current seen by the axons that are equidistant and orthogonal from the surface of the electrode remains as uniform as possible while the nerve is stimulated. Stated differently, poor electric field coverage and weak injected current in the overlap region of the nerve's circumference results in fewer axons recruited in that region compared to the axons outside of the overlap region. Maintaining consistent injected current for axons equidistant and orthogonal from the electrode results in more uniform recruitment of the similar axons along the entire circumference of the stimulated area of the nerve ("similar" axons are discussed further below). Thus, an improved electrode will provide relatively uniform injected current around the entire circumference of the nerve. For example, the outermost axons in fascicle A nearest the overlap and the outermost axons in fascicles C and D farthest from the overlap have an injected current that is as similar as possible. It is considered desirable that the magnitude of injected current in axons that are of a similar orthogonal distance from the surface of the electrode is within about 25% of each other, and even more desirable to have the injected current be within 10%, of each other. In other words, referring to FIGS. 5 and 6, assuming that there are axons in fascicle A that are the same orthogonal distance from the surface of the electrode as axons in fascicles C and D, it is desirable that the magnitude of injected current in these axons be within about 25% (and even more desirably, within about 10%) of each other.

Figure 16A:
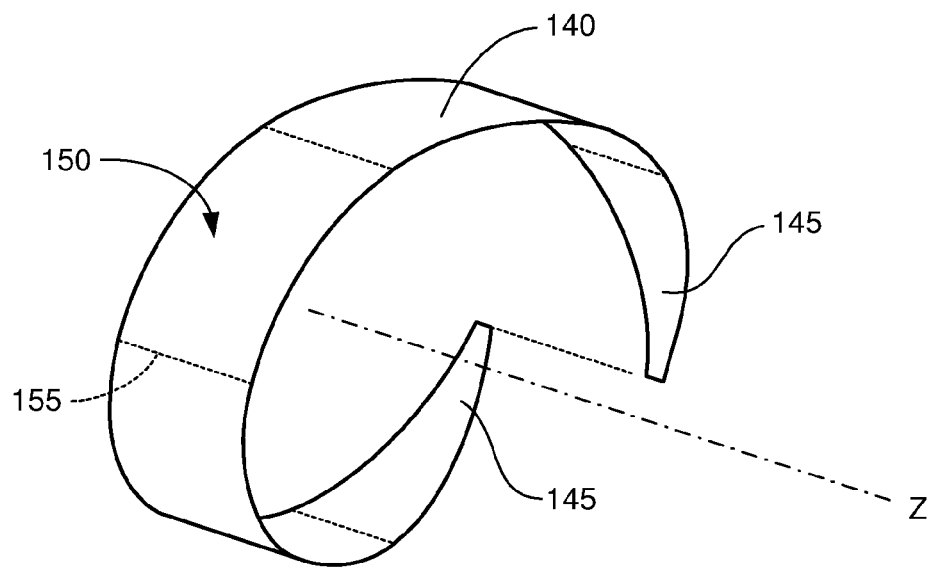
FIGS. 16A-B are perspective views of a conductor of a helical electrode that illustrate a plurality of equal sectors along the conductor.
Figure 16B:
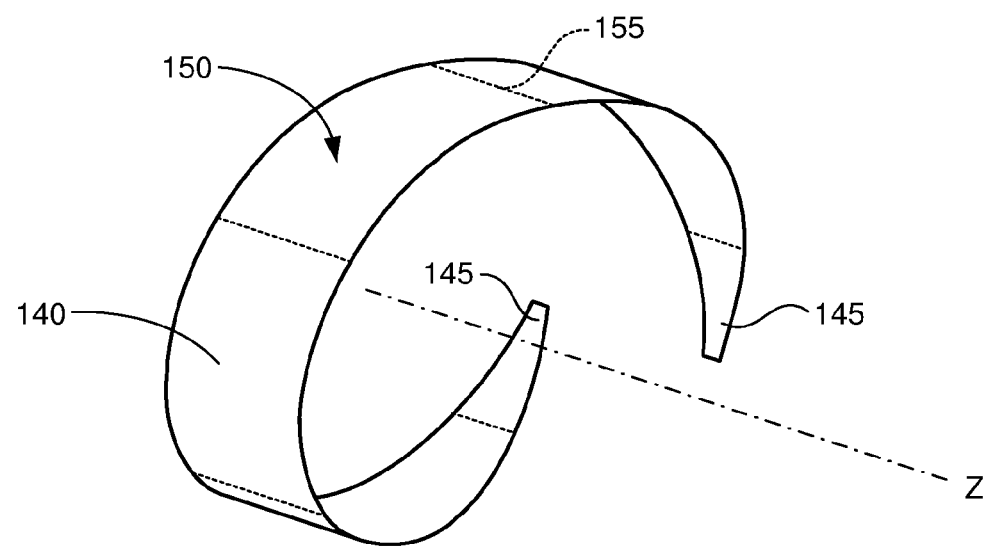
Figure 17A:
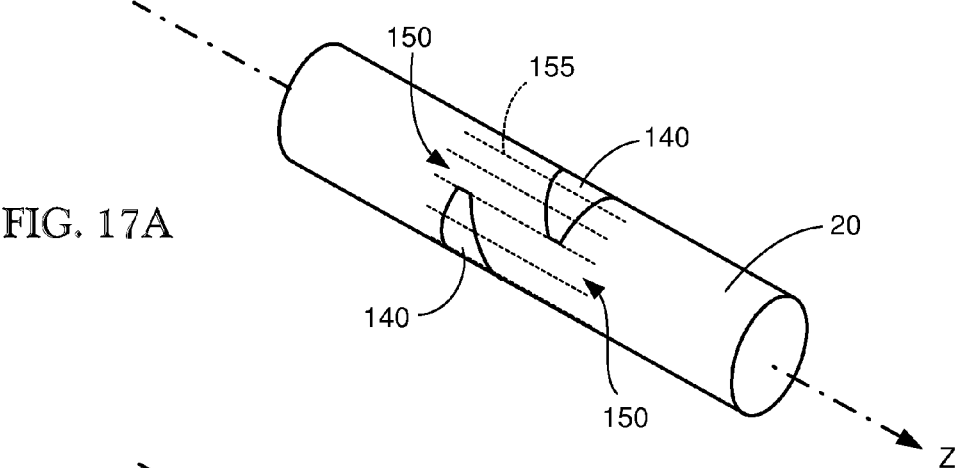
FIGS. 17A-C illustrate three different configurations of a helical electrode wrapped around a nerve with a plurality of equal sectors around the circumference of the nerve.
Figure 17B:
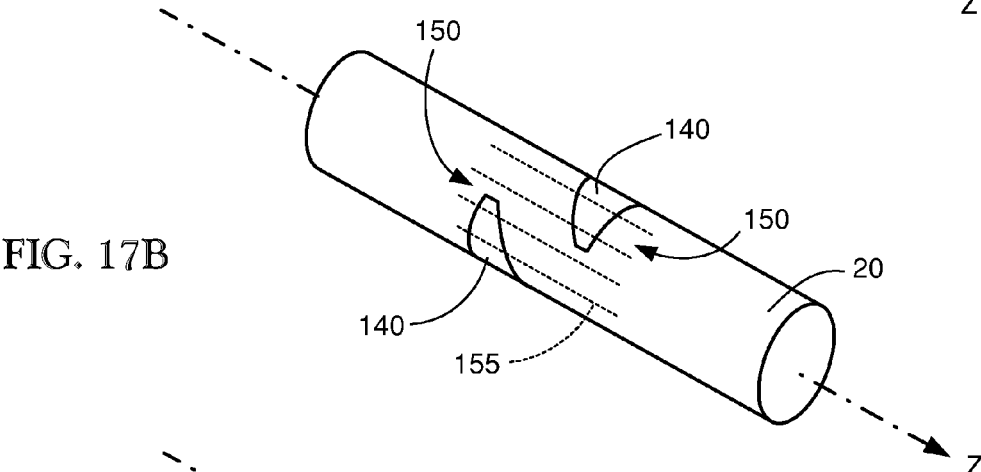
Figure 17C:
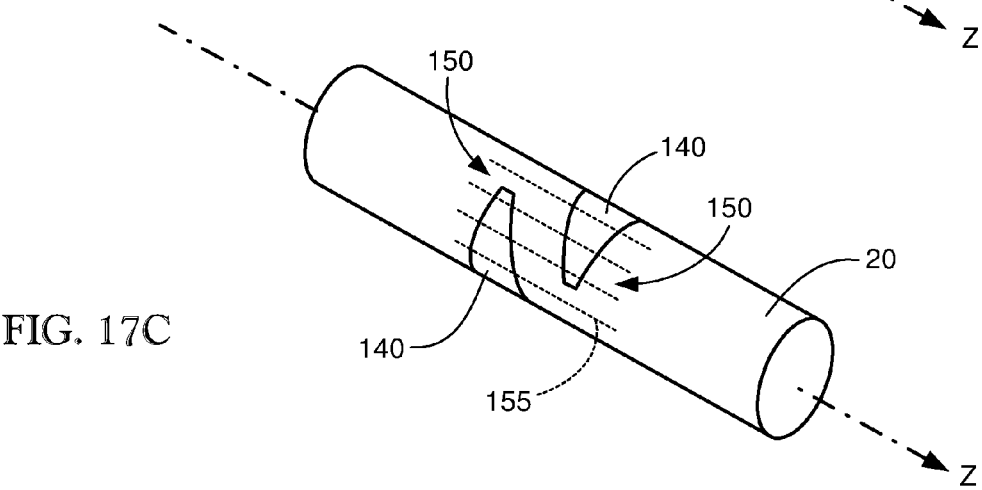

FIGS. 16 A-B each show an electrode 140 that is divided into a plurality of equal sectors 150, which are illustrated by dashed lines 155. The number of equal sectors 150 along the electrode 140 and the orientation of the equal sectors 150 are shown for illustrative purposes only. For example, the edge of one of the equal sectors 150 may be aligned with an end section 145 of the electrode 140, as shown in FIG. 16A. Alternatively, one of the equal sectors 150 may overlap the end sections 145 of the electrode 140, as shown in FIG. 16B. FIGS. 17 A-C show three different configurations of an electrode 140 wrapped around a circumference of a nerve 20. The nerve 20 may be divided into a plurality of equal sectors 150, which are illustrated by dashed lines 155. The number of equal sectors 150 along the nerve 20 as well as the orientation of the equal sectors 150 may be varied as shown in FIGS. 17 A-C. The electrical conductor 140 may produce an electric field in which the injected current or the peak value of the second spatial derivative of the electric field applied in each of the equal sectors 150 varies by no more than about 25%. Further, the electrical conductor 140 may produce an electric field in which the injected current applied in each of the equal sectors 150 varies by no more than about 10%. As evident in FIGS. 16A, 16B, and 17A-17C, the ability to compare the injected current or electric fields applied in the equal sectors 150 is not affected by defining the equal sectors 150 as sectors of the electrical conductor 140 or sectors of the nerve 20—both definitions are effectively the same because they do not change the math involved in comparing the sectors.

Figure 9:
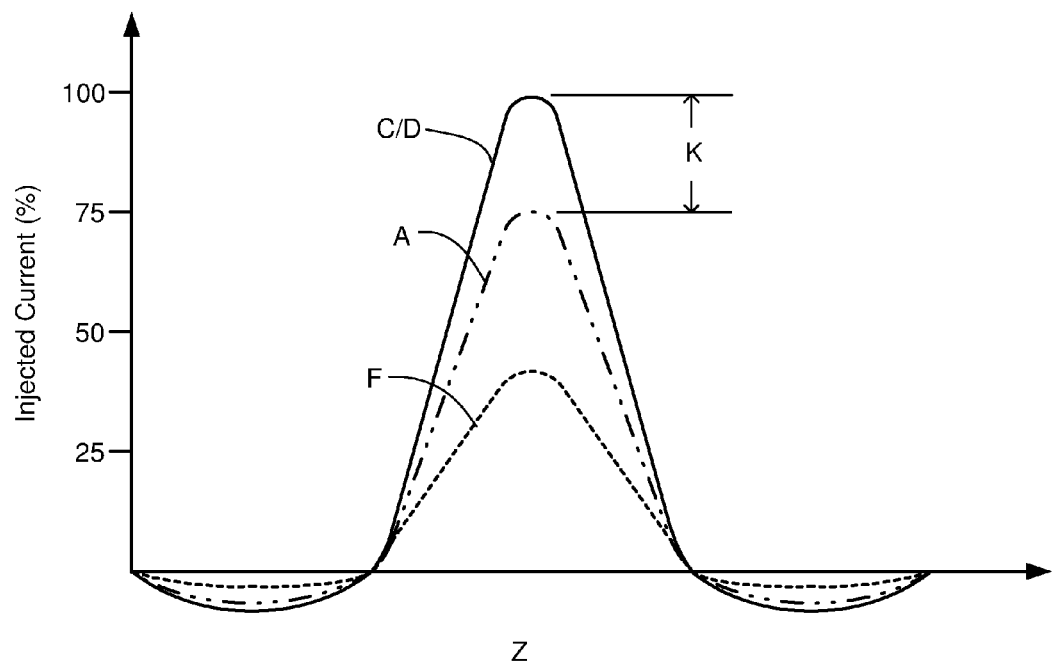
FIG. 9 is a graph of injected current versus position along the longitudinal axis for nerve fibers nearest and farthest away from the overlap area of a helical nerve stimulation electrode.

FIG. 9 shows a graph of injected current versus position along the longitudinal Z-axis for three fascicles of FIGS. 5 and 6 in different positions relative to the conductor overlap area. The curve with the highest peak, labeled C/D, represents the injected current in the axons located within fascicles C and D (recall that each fascicle contains numerous axons). These are the outer fascicles farthest from the overlap area, and therefore experience a higher peak injected current because the electric field is strong and uniform relative to the field applied at the overlap area. However, the curve labeled A represents the injected current for the axons within fascicle A, which is closest to the overlap area. Because it is near the overlap area, the effect of the conductor ends on the electric field reduces the peak injected current for the axons in this fascicle. Corresponding curves for fascicles B and E are not shown in FIG. 7, but will have peaks that fall close to or below curve C/D, but above curve A. The lowest of the curves is labeled F and represents the injected current for the central fascicle F, shown in FIGS. 5 and 6. The axons in this fascicle experience the lowest peak injected current because of its overall distance from the conductor and the intervening nerve structure and tissue.

In reality, the curves in FIG. 9 represent a somewhat simplified model of the actual injected current experienced by the axons. The amount of injected current experienced by each axon is highly dependent on the distance from the electrode to the axon. The closer the axon is to an electrode, the better the electrode "recruits" the axon by injecting current into it. Thus, within any fascicle, the axons closest to the electrode will be recruited better than axons within the same fascicle residing closer to the center of the nerve and further from the electrode. It is possible, however, to compare injected current throughout the nerve by comparing the injected current in axons that are approximately equidistant from the electrode. Therefore, the comparison of the injected current in curves A and C/D in FIG. 9 accurately represents the difference in injected current between equidistant axons.

It can be seen from FIG. 9 that the peak injected current for axons within fascicle A is lower than the peak injected current for axons within fascicle C/D by some amount K. This overall difference K between the highest and lowest peak injected current for these axons that are approximately equidistant from the electrode can be expressed as a percentage. As discussed above, the inventor has determined that for effective nerve recruitment it is desirable that the injected current in reasonably similar axons approximately equidistant and orthogonal from the electrode be within about 25%, and more particularly within about 10%, of each other. A more consistent injected current leads to more effective nerve stimulation. To compare the injected current from one axon to the next, one must consider the similarity of the axons based on (i) their distance from the electrode and (ii) their type or class, which are addressed in the next two paragraphs.

First, an axon's ability to activate and conduct is highly dependent on its distance from the electrode because, according to Coulomb's law, the field strength is inversely proportional to the square of the distance between the axon and the electrode. If one uses the radial distance from the longitudinal axis (i.e., center) of the nerve to describe the equidistance of the axons, then this may not be accurate because non-uniform fibrous tissue growth between the nerve and the electrode would push some portions of the electrode further away from the nerve than other portions. Measuring the orthogonal distance from the surface of the electrode to the axons will compensate for fibrous tissue growth because the equidistant axons will change if tissue pushes the electrode sufficiently. Using the orthogonal distance helps to assure one is comparing equidistant axons (e.g., the accuracy of the comparison breaks down if one includes non-orthogonal axons relative to the ends of the electrode ribbon at gap Φ in FIG. 5). However, where fibrous tissue growth is minimized or is uniform, axons equidistant from the longitudinal axis of the nerve will behave sufficiently similar when they experience a uniform applied field.

Second, axonal behavior depends strongly on the axon's class and diameter. Axons with a larger diameter carry significantly more current than smaller diameter axons (comparable to current flowing in copper cables). Two important factors in an axon's ability to conduct current are its diameter and degree of myelination. The vagus nerve contains three classes of nerve fibers (A, B, and C), which are classified by their diameter and conduction velocity. These classes are commonly referred to as "nerve fiber types" or "nerve fiber classes," but are also known as "axon type" or "axon class" (and are used herein interchangeably). Table 1 below shows the differences between the three types of axons. The vagus nerve contains approximately 80,000 to 100,000 nerve fibers, but about 80% of these are unmyelinated C fibers (which are difficult to recruit). The remaining 20% are myelinated A and B fibers, which are the principal fibers recruited in VNS therapy. This 20% of recruitable A and B fibers consists of approximately 16% small fibers ($\leq 3$ μm (both A and B fibers)), roughly 3% medium fibers (3-9 μm (only A fibers)), and about 1% large fibers ($\geq 10$ μm (only A fibers)). It is important to note that not every equidistant axon will be recruited and "fire" when an electric field or current is applied to the nerve (i.e., the membrane potential is depolarized sufficient to cross the threshold potential, resulting in an action potential). Axons may not fire because their neuron is atypical, abnormal, damaged, unmyelinated, or simply a different fiber type (e.g., neurons in the vagus are A, B, or C fibers with varying axonal diameters, conduction velocities, conduction directions, and degrees of myelination). But for those similar equidistant axons that do fire properly, good recruitment will result in those axons having injection currents within about 25%, and more particularly within about 10%, of each other.

TABLE 1

| Axon Type | Axon Diameter (μm) | Myelinated? | Conduction Speed (m/sec) | Afferent or Efferent? |
|---|---|---|---|---|
| A | 1-22 | Yes | 5-120 | Both |
| B | $\leq 3$ | Yes | 3-15 | Efferent |
| C | 0.3-1.2 | No | 0.6-2.3 | Both |

The inventor has identified at least two features that can be included in a VNS electrode to make the injected current more consistent in the outer axons and thereby increase the effectiveness of the therapy. First, the inventor has determined that an electrode conductor that encircles the nerve about 360° is more effective than a conductor that encircles the nerve more or less than about 360°. In other words, it is desirable to have the helical conductor encircle the nerve as close to 360° as possible. This configuration is illustrated in FIGS. 3 and 4, where the full width end sections 46a, 46b, of the conductor substantially align with each other, surrounding the nerve by about 360°. The inventor has found that this configuration provides more effective stimulation of the axons in the overlap area near the ends of the conductor, and that both the gap and overlap conditions (FIGS. 5 and 6, respectively) decrease concentration of the electric field in the overlap area. As noted above and illustrated in FIG. 7, evidence from the inventor's modeling has shown that the axons near the ends of the conductor (e.g. axons in fascicle A in FIGS. 5 and 6) are stimulated less effectively than axons that are farther away from the ends (e.g. axons in fascicles C and D in FIGS. 5 and 6). Nevertheless, adjusting the circumference of the helical conductor to about one revolution can cause the difference in stimulation to fall within the desirable 25% range.

The inventor has found that an electrode encircling the nerve 360° can improve stimulation in the area of overlap. However, the effectiveness of this configuration is sensitive to the other dimensions of the electrode (pitch, electrode width, etc.) and can be insufficient in some circumstances to cause the difference in injected current to be within the desirable 25% range. The inventor has further found that while 360° is more effective for some configurations, creating a small gap condition with an electrode that encircles by about 330° can be more effective for others. Also, it has been found that a small gap condition is usually more effective than overlap condition (θ>360). Therefore, it is believed that the electrode should encircle approximately 330° to 360° for best stimulation (with a counter-tapered electrode).

In order to substantially fully surround the nerve without over-surrounding it, the actual circumferential extent of the conductor can vary from 360° at the time of manufacture and at the time of implantation. The diameter of a nerve 20 can increase due to post implantation swelling and tissue ingrowth. For example, in some prior electrode configurations, a 2 mm inner diameter electrode having θ=330° before implantation provided a final circumferential coverage of approximately 270° after implantation and tissue ingrowth, representing a decrease of about 22%. The inventor has determined that for a 2 mm diameter electrode of about 0.8 mm constant width, to provide a final circumferential coverage of about θ=360°, the initial circumferential extent of the conductor at the time of manufacture can be approximately 440°.

It is also to be recognized that the vagus nerve does not have the same diameter in all patients. The inventor's research has shown that even small variations in nerve size, which have the effect of changing the circumferential coverage of the electrode, can significantly affect stimulation within this region. Consequently, electrodes with several different lead sizes, other than 2 mm and 3 mm diameters mentioned specifically above, can be made to accommodate different patients. To accommodate tissue ingrowth and other factors, the circumferential extent of the conductor prior to implantation can also vary in electrodes of different sizes, in order to provide the desired coverage after implantation.

Another electrode design feature that the inventor has determined improves the effectiveness of the electrode conductor, and narrows the range of variation of injected current between axons near and away from the overlap area, relates to the geometry of the end sections of the electrode. That is, providing tapered end sections on the conductor, so that the end sections are narrowed, also improves the effectiveness of the electrodes by concentrating the electric field in the region of the conductor ends. Various approaches to and features of tapering the conductor ends are illustrated in FIGS. 10-15.

Figure 10:
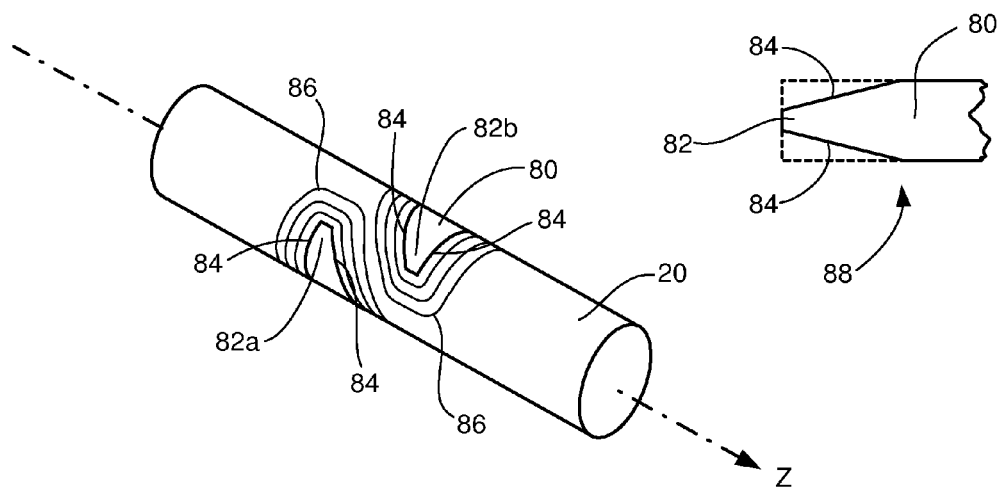
FIG. 10 is a perspective view of a portion of a nerve showing a centrally-tapered helical conductor and field lines representing the electric fields from the ends of the conductor in the overlap region.

Shown in FIG. 10 is a portion of a nerve 20 having a helical electrode 80 wrapped around it by approximately one revolution. This electrode has end sections 82*a, b* that are centrally-tapered. That is, both lateral sides edges 84 of the conductor are tapered toward the longitudinal center of the conductor, as conceptually shown in the detail view indicated generally at 88. The centrally-tapered conductor ends produce a more concentrated electric field in the overlap region, represented by the radiating field lines 86. Additionally, depending upon the pitch P of the helix, the ends of the conductor can also be longitudinally separated by a distance that reduces interference between the conductor ends. This approach can be used for both tapered and non-tapered conductors, and is suggested by the gap between the groups of radiating field lines 86 associated with each of the respective conductor ends in FIG. 8.

Figure 11:
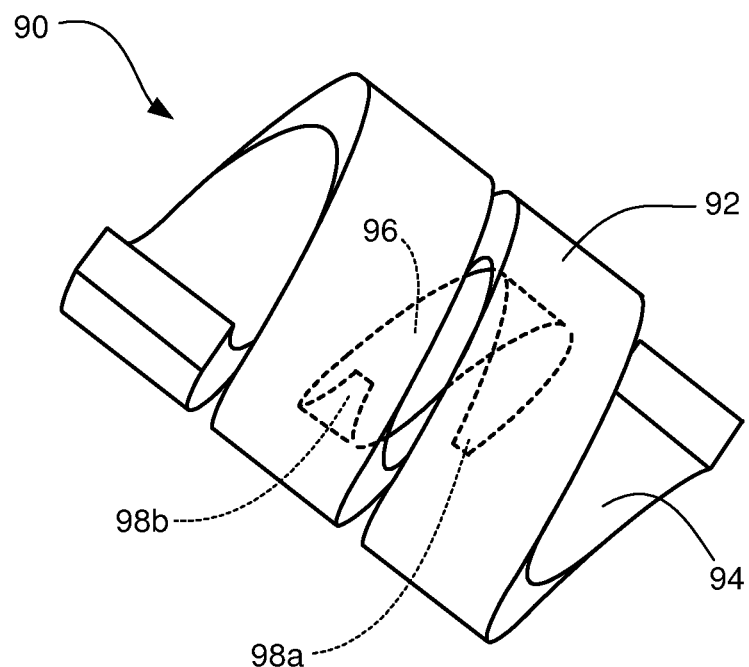
FIG. 11 is a perspective view of another embodiment of a helical electrode suitable for nerve stimulation, the conductor having counter-tapered end sections.
Figure 12:
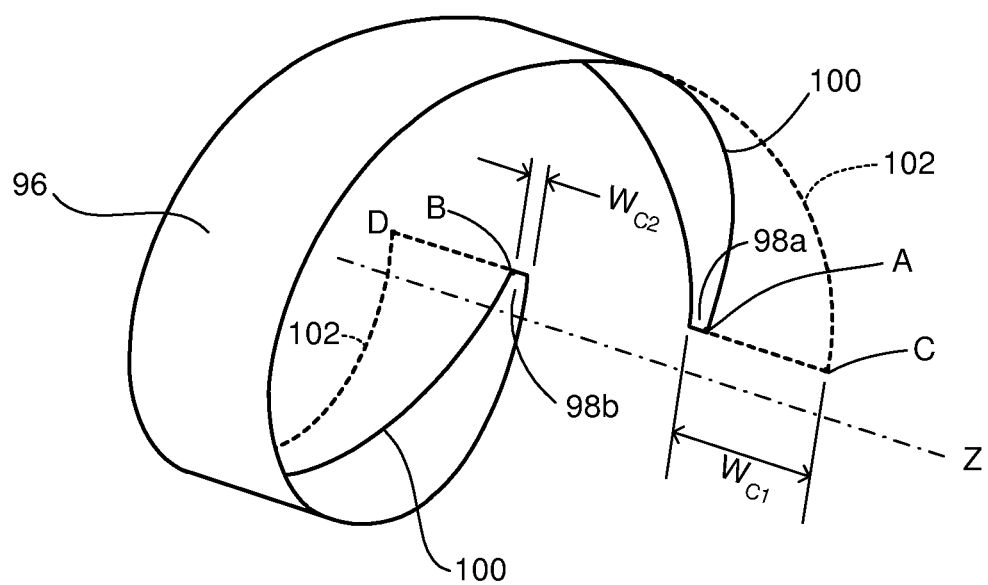
FIG. 12 is a perspective view of the conductive ribbon of the helical electrode of FIG. 11.

Another embodiment of a conductor having tapered end sections is shown in FIGS. 11 and 12. Shown in FIG. 11 is a helical electrode 90 (similar to that of FIG. 3) having a helical substrate 92 that defines an inner surface 94. A helical conductor 96 is disposed upon the inner surface, and includes counter-tapered end sections 98*a, b*. A perspective view of this electrode is shown in FIG. 12.

As shown in FIG. 12, the end sections 98 are tapered on one side only from the full width $W_{C1}$, the full width of the conductor 96, to a narrower width $W_{C2}$ at their extreme distal ends. The tapered side edges of the conductor are labeled 100. The extreme ends 98*a, b* of conductor 96 taper in from the full width $W_{C1}$ of the conductor, to a narrower width $W_{C2}$. A theoretical outline of the end of the conductor if it were not tapered is shown in dashed lines at 102 As with the embodiment of FIG. 8, the narrower, tapered end sections have the effect of concentrating the electric field in the overlap area, thus helping to counter the effect of the helical offset of the end sections.

Additionally, in the embodiment of FIG. 12, the ends 98 of the conductor taper in opposing directions. The opposing direction of the tapers causes the longitudinal distance between extreme edges of opposing ends of the conductor 96 to be reduced (measured parallel to the Z-axis of the helix). The term "extreme edges of opposing ends of the conductor" has reference to points at the ends of the conductor that are furthest distant from each other when the conductor is coiled in its helical configuration. In FIG. 12 these points are labeled A and B. If the conductor had a substantially constant width from end to end and no tapers, the extreme edges of opposing ends of the conductor would be located at points C and D. By narrowing the ends of the conductor and bringing their extreme portions closer together, the effectiveness of the electric field is increased in the overlap area.

The length and magnitude of the taper can vary. In one embodiment, with a conductor 96 having a maximum width $W_{C1}$ of about 0.8 mm, the minimum width $W_{C2}$ of the conductor at the end of taper can be about 0.04 mm, or about 1/20 of the maximum width. The inventor believes that tapers that reduce the width of the conductor by about 3/4 to 9/10 of its maximum width are desirable.

Figure 13:
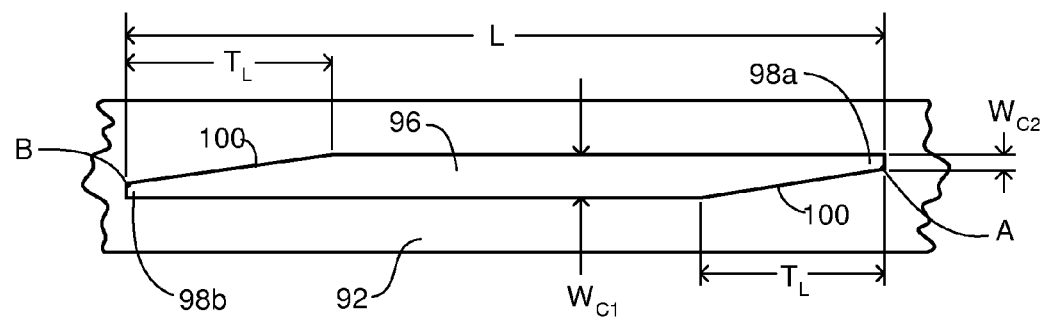
FIG. 13 is a partial, flattened-out planar view of a helical electrode like that of FIG. 12, showing one embodiment of a conductive ribbon with counter-tapered opposing end sections.

As shown in FIG. 13, the length $T_L$ of each taper represents some portion of the total length L of the conductor 96. In one embodiment, the inventor has used a conductor having tapered end sections with a taper length $T_L$ that is about one fourth the total length L of the conductor, so that about half the total length of the conductor is tapered, while the remainder is substantially full width. Where the conductor is sized to encircle the nerve with a circumferential coverage of about 360°, this causes the constant width portion of the conductor to extend along about 180° of the conductor, and the tapered portions to occupy about 90° of the conductor's circumferential extent at each end. Other taper proportions can also be used. For example, it is believed that individual tapers of 1/8 to 1/3 of the total length of the conductor can be used.

Figure 14:
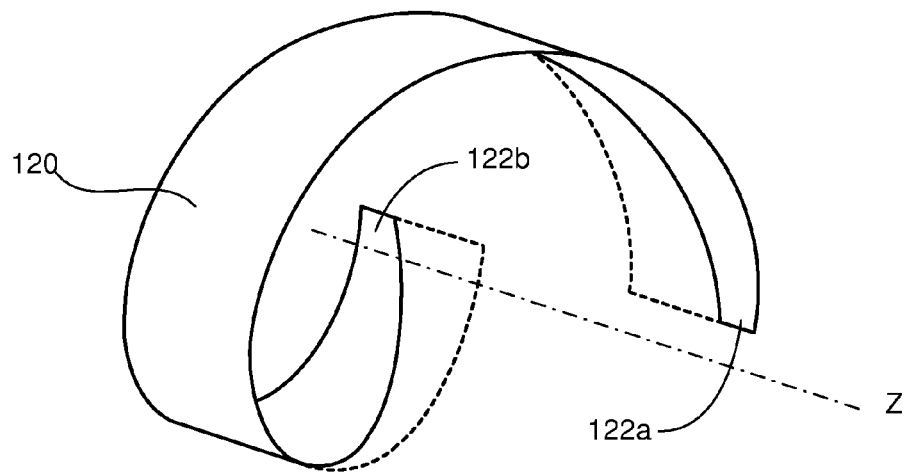
FIG. 14 is a perspective view of a conductor of a helical electrode like that of FIG. 12, but having an oppositely oriented counter taper of the conductor ends.

While the helical conductor 96 shown in FIGS. 9-13 has counter-tapered end sections 98 that taper toward each other, it is believed that other tapered configurations can also be useful. Shown in FIG. 14 is a conductor 120 having counter-tapered end sections 122*a, b* that taper away from each other. By tapering the ends of the conductor away from each other, the electric field created near the overlap area will consist of two distinct regions at each end of the electrode. Each region will have a concentrated change in the electric field along the Z-axis, representing the length of the nerve which will increase axon activation in the region near the ends of the ribbon. Tapering the conductor ends away from each other also has the effect of separating the competing electric fields, thus reducing or preventing overlap of the fields and providing two concentrated fields along the axis of the nerve. This helps reduce spreading of the field along the axis of the nerve in the overlap area, as discussed above.

It is to be appreciated that other tapered arrangements can also be applied to the ends of the conductor, in addition to those shown herein. For example, while the tapers shown in FIGS. 10-14 are linear or straight-line tapers, other, non-linear taper configurations can also be used, such as curved, etc. Other adjustments to the end geometry of the conductor can also be applied. Tapering the conductor, whether centrally-tapered (as in FIG. 10), counter-tapered (as in FIGS. 12 and 14) or otherwise, helps improve nerve recruitment in the overlap region, and is believed to have little effect on the rest of the nerve, except for possibly a slight increase in recruitment of other nerve fibers due to the increase in the surface charge density on the ribbon.

Figure 15A:
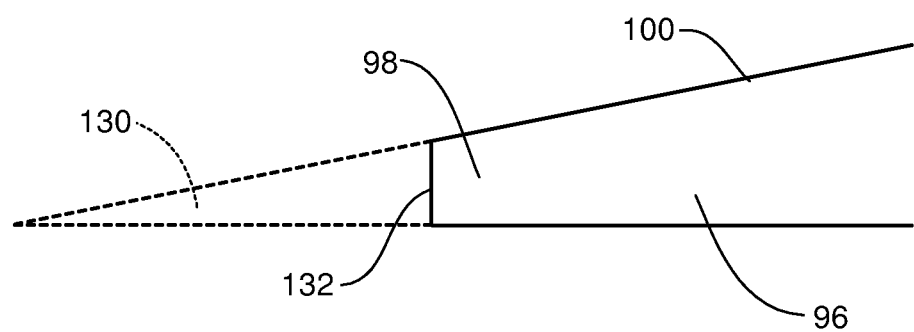
FIGS. 15A-C are detail views showing three different ways in which the distal tapered end sections of the conductor can be truncated.
Figure 15B:
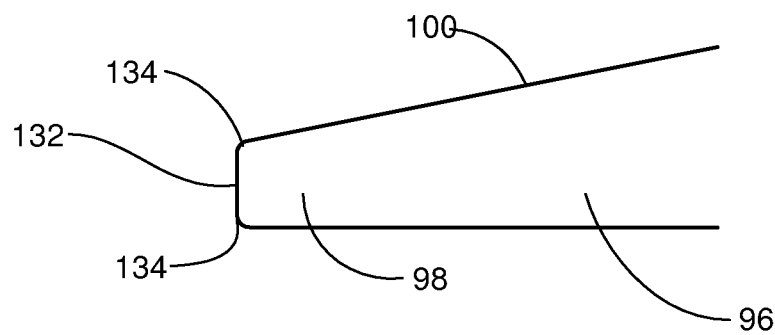
Figure 15C:
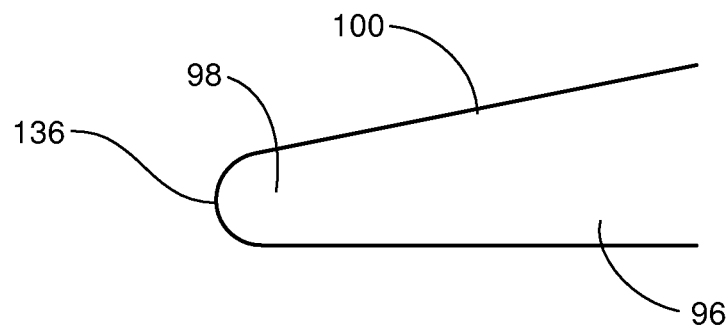

The inventor has also found that it is desirable to truncate the tapered ends of the conductor. The tapered end sections can be truncated in a variety of ways. Several truncation configurations are illustrated in FIGS. 15A-15C. These figures have reference to the embodiment shown in FIGS. 11-13, and represent a detail view of the left end of the conductor 96 of FIG. 13, in the vicinity of point B. As shown in FIG. 15A, the end section 98 of the conductor 96 can simply be truncated straight across the width of the conductor, from what would otherwise be a sharp pointed end 130, to have a flattened end 132. In another embodiment, a truncated end can have rounded corners 134 on opposing extremes of a flattened end 132, as shown in FIG. 15B. As yet another embodiment, the extreme end 98 of the conductor can be provided with an entirely rounded end profile 136, as shown in FIG. 15C. Truncation or rounding of the ends of the conductor can also be applied to non-tapered conductors, such as are shown in FIGS. 3-4. These and other methods of truncating the extreme end of the conductor can be used to modify the geometry of the end of the conductor. Truncating or rounding and smoothing the extreme ends of the conductor has the effect of reducing high current densities that tend to form near sharp points on electrodes.

The features described herein provide an electrode for nerve stimulation that can provide effective stimulation while using less power than prior helical electrodes. By providing a conductor that surrounds the nerve by about 360°, the amplitude of the electric field in the overlap region is increased. The conductor can also have tapered end sections, so that the electric field in the overlap area of the conductor is concentrated, and provides more consistent stimulation of the axons within a nerve. In particular, the configuration of the helical conductor causes injected current in axons that are orthogonal and equidistant from the surface of the electrode and near the helical overlap area to be within about 25% (or, within about 10%) of injected current in similar axons elsewhere (similar in their orthogonal distance from the electrode and axon type). The features of setting the circumferential extent of the conductor to about one revolution and tapering the ends of the conductor can be used together or independently, and still be effective, though it is believed that their effectiveness is increased when both of these features are used together. Likewise, truncation or smoothing and rounding of the ends of the conductor can be used whether the conductor is tapered or not. Additionally, while the helical electrode disclosed herein is described in terms of its use for vagus nerve stimulation, it is to be understood that this electrode, in various embodiments, can also be applied to other nerve stimulation applications.

Although various embodiments have been shown and described, the invention is not so limited and will be understood to include all such modifications and variations as would be apparent to one skilled in the art. For example, equivalent elements may be substituted for those specifically shown and described, certain features may be used independently of other features, and the number and configuration of various components described above may be altered, all without departing from the spirit or scope of the invention as defined in the appended claims.

Such adaptations and modifications should and are intended to be comprehended within the meaning and range of equivalents of the disclosed exemplary embodiments. It is to be understood that the phraseology of terminology employed herein is for the purpose of description and not of limitation. Accordingly, the foregoing description of the exemplary embodiments of the invention, as set forth above, are intended to be illustrative, not limiting. Various changes, modifications, and/or adaptations may be made without departing from the spirit and scope of this invention.

What is claimed is:

1. A helical electrode for nerve stimulation, comprising:
   an insulative helical substrate having an inner surface, the insulative helical substrate configured to wrap around a nerve; and
   an electrical conductor disposed upon the inner surface, the electrical conductor having a first end portion, a second end portion opposite the first end portion, and a middle portion between the first end portion and the second end portion, the middle portion having a middle width, the electrical conductor defining a helix of about one revolution, the helix of about one revolution forming an overlap area where at least a portion of the first end portion and the second end portion longitudinally overlap, wherein the first end portion narrows from the middle width to a first width in a first direction away from the middle portion and the second end portion narrows from the middle width to a second width in a second direction away from the middle portion.

2. The helical electrode in accordance with claim 1, wherein the electrical conductor is further configured to produce an electric field in which a first injected current varies by no more than about 10% from a second injected current.

3. The helical electrode in accordance with claim 1, wherein the first width and the second width have similar width.

4. The helical electrode in accordance with claim 1, wherein the first width and the second width have different widths.

5. The helical electrode in accordance with claim 1, wherein the first end portion and the second end portion are counter-tapered.

6. The helical electrode in accordance with claim 1, wherein each taper comprises about one fourth a length of the conductor, and reduces a width of the conductor by about ⅛.

7. The helical electrode in accordance with claim 1, wherein the electrical conductor comprises truncated end sections.

8. The helical electrode in accordance with claim 1, wherein the substrate defines the helix having a pitch of about 1 mm/turn to about 2.5 mm/turn and a central insulation aperture having a diameter from about 2 mm to about 3 mm.

9. The helical electrode in accordance with claim 1, wherein the electrical conductor is a material including at least one of platinum, platinum/iridium alloy, iridium oxide, titanium nitride, tantalum and tantalum oxide.

10. The helical electrode in accordance with claim 1, wherein the electrical conductor defines the helix of more than one revolution before implantation which accommodates for post-implantation expansion of the nerve.

11. The helical electrode in accordance with claim 1, wherein the electrical conductor defines the helix of about 330° to about 375° after implantation.

12. A helical electrode for nerve stimulation, comprising:
   an insulative helical substrate having an inner surface, the insulative helical substrate configured to wrap around substantially an entire circumference of a nerve,
   wherein an entire circumference of the insulative helical substrate is divided into a plurality of equal sectors; and
   an electrical conductor disposed upon the inner surface, the electrical conductor defining a helix of about one revolution, the electrical conductor configured to produce an electric field via an energy source in which a peak value of a second spatial derivative of the electric field applied in each of the plurality of equal sectors varies by no more than about 25%.

13. The helical electrode in accordance with claim 12, wherein the electrical conductor is further configured to produce the electric field in which the peak value of the second spatial derivative of the electric field applied in each of the plurality of equal sectors varies by no more than about 10%.

14. The helical electrode in accordance with claim 12, wherein the electrical conductor further comprises tapered end sections.

15. The helical electrode in accordance with claim 14, wherein the tapered end sections are counter-tapered.

16. The helical electrode in accordance with claim 14, wherein each taper comprises about one fourth a length of the electrical conductor and reduces a width of the electrical conductor by about ⅛.

17. The helical electrode in accordance with claim 12, wherein the substrate defines the helix having a pitch of about 1 mm/turn to about 2.5 mm/turn and a central insulation aperture having a diameter from about 2 mm to about 3 mm.

18. The helical electrode in accordance with claim 12, wherein the electrical conductor defines the helix of about 330° to about 375° after implantation.

19. A helical electrode for nerve stimulation, comprising:
an insulative helical substrate having an inner surface, the insulative helical substrate configured to wrap around a nerve; and
an electrical conductor characterized by a length and a width and disposed upon the inner surface so as to be adjacent to the nerve, the electrical conductor defining a helix of about one revolution, the electrical conductor having a middle section of uniform width and end sections that taper to a width narrower than the uniform width of the middle section.

20. The helical electrode in accordance with claim 19, wherein the tapered end sections are counter-tapered such that a longitudinal distance between extreme edges of opposing ends of the electrical conductor is reduced.

* * * * *